US007054691B1

(12) United States Patent
Kuzma et al.

(10) Patent No.: US 7,054,691 B1
(45) Date of Patent: May 30, 2006

(54) PARTITIONED IMPLANTABLE SYSTEM

(75) Inventors: Janusz A. Kuzma, Parker, CO (US); Michael A. Faltys, Northridge, CA (US)

(73) Assignee: Advanced Bionics Corporation, Valencia, CA (US)

( * ) Notice: Subject to any disclaimer, the term of this patent is extended or adjusted under 35 U.S.C. 154(b) by 510 days.

(21) Appl. No.: 10/346,482

(22) Filed: Jan. 17, 2003

Related U.S. Application Data

(63) Continuation-in-part of application No. 10/038,041, filed on Jan. 2, 2002, now abandoned.

(51) Int. Cl.
*A61N 1/00* (2006.01)

(52) U.S. Cl. .......................................... 607/57; 607/36

(58) Field of Classification Search .................. 607/32, 607/36, 55–57, 60, 61, 65
See application file for complete search history.

(56) References Cited

U.S. PATENT DOCUMENTS 3,752,939 A 8/1973 Bartz
4,357,497 A 11/1982 Hochmair et al.
4,495,917 A 1/1985 Byers
4,516,820 A 5/1985 Kuzma
4,532,930 A 8/1985 Crosby et al.
4,592,359 A 6/1986 Galbraith
4,679,560 A 7/1987 Galbraith
4,764,132 A 8/1988 Stutz, Jr.
4,947,844 A 8/1990 McDermott
5,603,726 A 2/1997 Schulman et al.
5,776,172 A 7/1998 Schulman et al.
5,888,187 A 3/1999 Jaeger et al.
6,067,474 A 5/2000 Schulman et al.
6,216,040 B1 4/2001 Harrison
6,272,382 B1 8/2001 Faltys et al.
6,308,103 B1 10/2001 Gielen
6,473,651 B1 10/2002 Kuzma et al.

*Primary Examiner*—Scott M. Getzow
(74) *Attorney, Agent, or Firm*—Bryant R. Gold; Victoria A. Poissant

(57) ABSTRACT

An implantable system includes a plurality of implantable devices that are detachably coupled to each other. Each implantable device of the system includes: (1) an hermetically-sealed case housing electronic components; (2) feedthru terminals mounted to a wall of the hermetically-sealed case adapted to allow electrical contact from a location outside the hermetically-sealed case with the electronic components housed inside the hermetically-sealed case; (3) a coil external to the hermetically-sealed case attached to the feedthru terminals; (4) a flexible molding bonded to the hermetically-sealed case, and wherein the coil is embedded within or otherwise attached to the flexible molding; and (5) engagement means for engaging the flexible molding with a flexible molding of another implantable device of the implantable system. Such engagement means also aligns the coils of the implantable devices that are thus engaged with the engaging means to allow electromagnetic coupling to occur between the aligned coils. In one embodiment, the engaging means includes a hole formed in the flexible molding of a first implantable device and a knob portion formed in the flexible molding of a second implantable device, wherein the knob portion is sized to fit within the hole, and wherein when the knob portion is placed within the hole, the coil of the first device is coaxially aligned with the coil of the second implantable device.

13 Claims, 8 Drawing Sheets

PARTITIONED IMPLANTABLE SYSTEM

The present application is a continuation-in-part (C.I.P.) of U.S. patent application Ser. No. 10/038,041, filed 2 Jan. 2002, to be abandoned.

FIELD OF THE INVENTION

The present invention relates to implantable devices and systems, and more particularly, to a fully implantable device or system for stimulating or sensing living tissue, or for performing some other therapeutic function, wherein the implantable device or system includes partitioning the circuit functions within the implantable system in separate modules.

BACKGROUND OF THE INVENTION

Presently available implantable stimulation devices, such as a cochlear implant device or a neural stimulator, typically have an implanted unit, an external ac coil, and an external control unit and power source. The external control unit and power source includes a suitable control processor and other circuitry that generates and sends the appropriate command and power signals to the implanted unit to enable it to carry out its intended function. The eternal control unit and power source is powered by a battery that supplies electrical power through the ac coil to the implanted unit via inductive coupling for providing power for any necessary signal processing and control circuitry and for electrically stimulating select nerves or muscles. Efficient power transmission through a patient's skin from the external unit to the implanted unit via inductive coupling requires constant close alignment between the two units.

Representative prior art cochlear implant systems are disclosed, e.g., in U.S. Pat. Nos. 4,532,930; 4,592,359; 4,947,844 and 5,776,172, all of which are incorporated herein by reference. Fully implantable cochlear implant systems are shown, e.g., in U.S. Pat. Nos. 6,272,382 and 6,308,101, also incorporated herein by reference.

Disadvantageously, each of the known prior art cochlear stimulation systems, except those that are fully implantable, requires the use of an external power source and speech processing system, coupled to the implanted stimulation device. For many patients, achieving and maintaining the required coupling between the external components and the implanted component can be troublesome, inconvenient, and unsightly. Thus, there exists a need and desire for a small, lightweight fully implantable device or system that does not require an external unit in order to be fully functional, that does not need constant external power, and that includes a long-lasting internal battery that may be recharged, when necessary, within a relatively short time period.

Moreover, even if a rechargeable battery were available for use within an implantable cochlear stimulation system, such rechargeable battery must not significantly alter the size of the existing implantable cochlear stimulator. This is because the curvature and thickness of the skull is such that there is only a limited amount of space wherein a surgeon may form a pocket wherein a cochlear stimulator may be implanted. This is particularly an acute problem for young children, where the thickness of the skull is relatively thin and the curvature of the skull is greater than for an adult. Thus, there is a need for a fully implantable cochlear implant system that is adaptable and lends itself for implantation within a range of head sizes and shapes.

Additionally, even where a rechargeable battery is employed within a fully implantable cochlear implant system, which fully implantable system includes an implantable speech processor and microphone, it may be necessary or desirable, from time to time, to replace the battery and/or to upgrade the speech processor hardware. Because implantation of the cochlear implant system, including insertion of the delicate electrode array into the cochlea of the patient, represents major surgery, which major surgery would hopefully only need to be performed once in a patient's lifetime, it is seen that there is also a need for a fully implantable cochlear implant system wherein the battery and/or speech processor may be replaced or upgraded from time to time through minimal invasive surgery, while leaving the implantable cochlear stimulator and delicate cochlear electrode array intact for use with the replaced battery and/or upgraded speech processor.

Further, should the internal battery or speech processor within the implant system malfunction, or should the user desire not to use the internal battery or speech processor for certain time periods, there exists a need to be able to power and operate at least the stimulator portion of the implant system from an external power source so that the implant system can continue to operate and provide its intended cochlea-stimulation function until such time as a new battery and/or upgraded speech processor can be safely implanted, or for as long as desired. This affords the patient the flexibility to select when additional implant surgery, if any, is to be performed, without having to shut down operation of the existing implant system. That is, the existing implant system may thus continue to operate with the assistance of an external power boost and/or external speech processor, for as long as necessary.

SUMMARY OF THE INVENTION

The present invention addresses the above and other needs by providing an implantable system having at least two hermetically-sealed units or modules, each unit or module having a portion of the electronic circuitry and other components of the implantable system housed therein. Each hermetically-sealed unit further has a non-hermetically-sealed antenna coil attached to the circuitry housed within each unit through feed-through terminals. Such antenna coils are preferably embedded within a rubberized type of material, such as a silicone mold. The two or more units are coupled to each other by aligning the antenna coils so as to permit inductive or rf coupling to occur between the coils. Coupling through the antenna coils may also advantageously occur with an external device having an external antenna coil that can be placed on or near the skin over the location where the implanted coils are positioned.

In accordance with one aspect of the invention, an implantable system is provided that includes a plurality of implantable devices detachably coupled to each other. Each implantable device comprises: (a) an hermetically-sealed case housing electronic components; (b) feedthrough terminals mounted to a wall of the hermetically-sealed case adapted to allow electrical contact from a location outside the hermetically-sealed case with the electronic components housed inside the hermetically-sealed case; (c) a coil external to the hermetically-sealed case attached to the feedthrough terminals; (d) a flexible molding bonded to the hermetically-sealed case, and wherein the coil is embedded within the flexible molding; and (e) engagement means for engaging the flexible molding with a flexible molding of another implantable device of the implantable system, wherein the engagement means also aligns the coils of the implantable devices that are engaged with the engaging means to allow electromagnetic coupling between the aligned coils.

The present invention thus provides a fully implantable device or system for stimulating or sensing living tissue, or for performing some other therapeutic function, wherein the implantable device or system includes partitioning the circuit functions within the implantable system in separate modules. The partitioned system may include, for example, a rechargeable battery or other replenishable power source, in one module; and electronic stimulation circuitry in another module.

A key feature of the invention relates to housing the system components in two or more detachable modules. The use of detachable modules facilitates upgrading circuit functions, adapting the system to a range of applications and sizes, and/or replacing, through minimal invasive surgery, the battery or power source used within the system.

Another feature of the invention allows the implantable system to operate with conventional external (non-implanted) components traditionally used with such a system. For example, if the implantable system comprises a cochlear stimulation system, having a first module that houses a rechargeable battery and an implantable speech processor with implantable microphone, and a second module that houses an implantable cochlear stimulator (ICS), with attached cochlear lead, the present invention allows the ICS to also operate with a conventional external speech processor, and/or an external battery charger, when needed or desired.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

1.0 OVERVIEW

The present invention relates generally to a fully implantable system having two or more implantable modules that are coupled together. Typically, one module may house a rechargeable battery (or other power source). Such systems are described, including the rechargeable battery portion, in U.S. Pat. No. 6,308,101, previously incorporated herein by reference.

One embodiment of the present invention relates to an implantable cochlear stimulation system that is partitioned into two components: (1) a cochlear stimulator component and associated electrode array which are designed to last for the life of the patient; and (2) an implantable speech processor and battery component which are designed to be explanted and replaced from time to time. It is to be understood, however, that other embodiments of the invention may be used, For example, the present invention need not be partitioned as described above (wherein one component is a cochlear stimulator and the other component is a battery and speech processor) and need not be limited to just a cochlear stimulation system. Any medical or other device or system which must be implanted in living tissue, or a similar environment, and which requires the components of the system to be split into two or more modules that are connected together, may benefit from the application and teachings of the present invention.

Figure 1A:
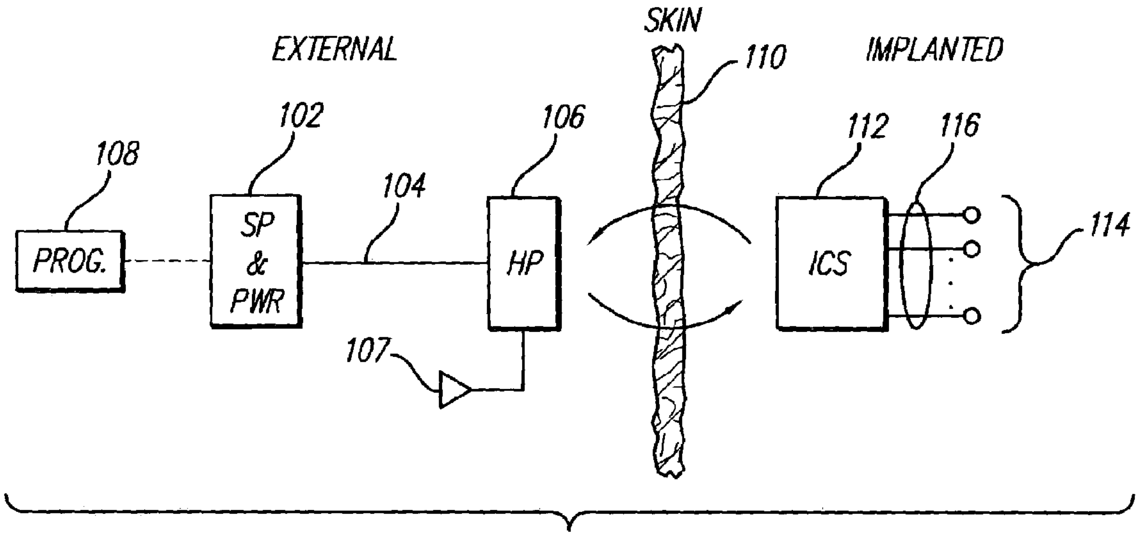
FIG. 1A illustrates a typical cochlear stimulation system as currently used by many patients, including an implantable cochlear stimulator (ICS) that is inductively coupled with an external headpiece (HP) connected with an external speech processor (SP) and power source.

To better understand and appreciate the present invention, it will be helpful to briefly review existing cochlear stimulation systems. Such review, representing the description of FIGS. 1A through 2D which follows, is taken, in large part from U.S. Pat. No. 6,272,382, incorporated herein by reference. Such description is generally representative of all tissue-stimulating systems. A representative cochlear stimulation system is fully described, e.g., in U.S. Pat. No. 5,776,172, incorporated herein by reference. As described in the '172 patent, and as illustrated in FIG. 1A, such existing system includes implanted and external components. The external components include a speech processor (SP), a power source (e.g., a replaceable battery), and a headpiece (HP) 106. The SP and power source are typically housed within a wearable unit 102 that is worn or carried by the patient. The wearable unit is electrically connected to the HP 106 via a cable 104. A microphone 107 is also included as part of the headpiece 106.

The implanted components include an implantable cochlear stimulator (ICS) 112 and an array of electrodes 114. The electrode array 114 is intended for implantation within the cochlea of the patient. The ICS 112 is implanted behind the ear, so as to reside near the scalp. The electrode array 114 is permanently connected to the ICS by way of a multi-conductor implantable cable 116.

Inside of the headpiece 106 is a coil that is used to inductively or magnetically couple a modulated ac carrier signal to a similar coil that is included within the ICS 112. In order to achieve efficient coupling, without suffering significant losses in the signal energy, it is important that the external coil within the headpiece be properly aligned with the internal coil inside the ICS. To achieve proper alignment, a magnet is typically included within both the headpiece 106 and the ICS 112, and the resulting magnetic attraction between the two magnets not only aligns the coils, as desired, but also provides a holding force that maintains the headpiece 106 securely against the scalp or skin 110 of the patient. Disadvantageously, the use of such a magnet may, for some patients, limit their ability to have magnetic resonance imaging (MRI) performed on them, at least in the vicinity of the head.

In use, a carrier signal is generated by circuitry within the wearable unit 102 using energy derived from the power source within the speech processor unit 102. Such carrier signal, which is an ac signal, is conveyed over the cable to the headpiece 106 where it is inductively coupled to the coil within the ICS 112. There it is rectified and filtered and provides a dc power source for operation of the circuitry within the ICS 112. Sounds are sensed through the external microphone 107, amplified and processed by circuitry included within the speech processor unit 102, and converted to appropriate stimulation signals in accordance with a selected speech processing strategy by circuitry within the speech processor unit 102. These stimulation signals modulate the carrier signal that transfers power to the ICS 112. The ICS includes an appropriate demodulation circuit that recovers the stimulation signals from the modulated carrier and applies them to the electrodes within the electrode array 114, The stimulation signals identify which electrodes, or electrode pairs, are to be stimulated, the sequence of stimulation and the intensity of the stimulation.

Some embodiments of the ICS 112, as indicated in the '172 patent, include a backtelemetry feature that allows data signals to be transmitted from the ICS 112 to the headpiece 106, and hence to the Speech Processor 102. Such backtelemetry data provides important feedback information to the speech processor regarding the operation of the ICS, including the amount of power needed by the ICS.

When adjustment or fitting or other diagnostic routines need to be carried out, an external programming unit 108 is detachably connected to the SP unit 102. Through use of the external programmer 108, a clinician, or other medical personnel, is able to select the best speech processing strategy for the patient, as well as set other variables associated with the stimulation process. See, e.g., U.S. Pat. No. 5,626,629, incorporated herein by reference, for a more detailed description of a representative fitting/diagnostic process.

The system shown in FIG. 1A has proven to be of great value and benefit to many patients who could not otherwise experience the sensation of hearing. Nonetheless, there are several drawbacks associated with use of the system. For example, the wearable unit 102 must be worn or carried by the patient, and the cable 104, which may be up to one meter long, must be routed from the unit 102 to the headpiece 106. Some patients find wearing the unit 102 to be inconvenient, and find the use of the headpiece 106, with its cable 104, to be unsightly and uncomfortable.

Figure 1B:
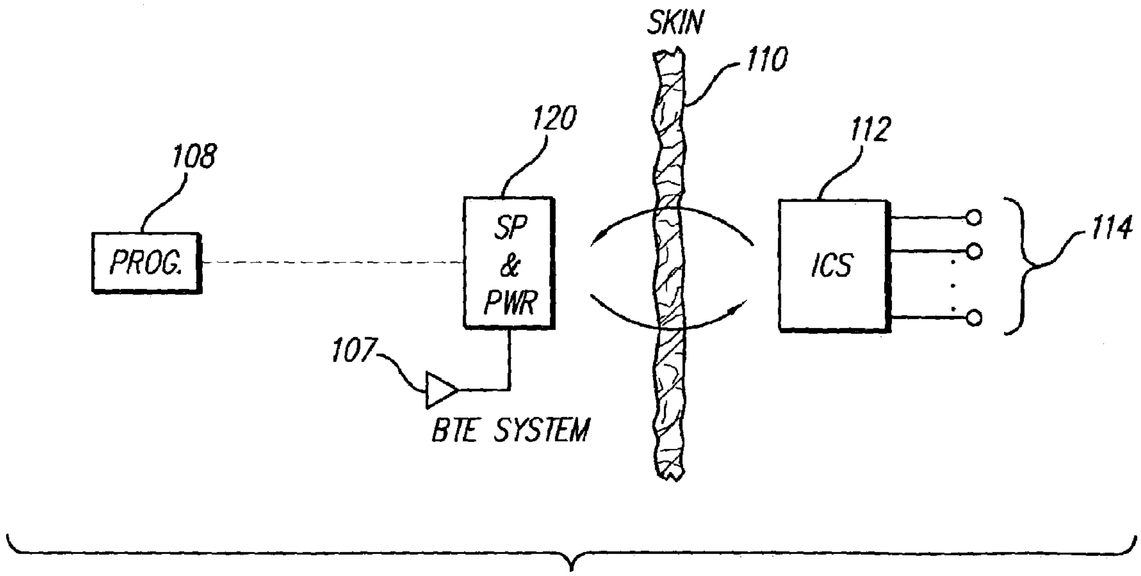
FIG. 1B illustrates a behind-the-ear (BTE) cochlear stimulation system that includes an implanted cochlear stimulator (ICS) and an external BTE unit that includes a power source, a speech processor and a microphone.

In order to eliminate the need for the cable 104, a behind-the-ear (BTE) unit 120 is also available, as illustrated in FIG. 1B. The BTE unit 120 includes everything previously included within the wearable unit 102, only in a much smaller volume. The BTE unit 120 thus includes a suitable power source, as well as the circuitry needed for performing a desired speech processing function. With the BTE unit 120, there is thus no need for the cable 104, and the patient simply wears the BTE unit behind his or her ear, where it is hardly noticed, especially if the patient has hair to cover the BTE unit.

Advantageously, the batteries employed within the wearable unit 102 (FIG. 1A) or the BTE unit 120 (FIG. 1B) may be readily replaced when needed. Still, the BTE unit 120 may become uncomfortable to wear when worn for long periods of time, and must be removed at certain times, such as when swimming or bathing. Some patients would thus like the convenience of being able to hear at all times, including when swimming or bathing, and thus a fully implantable stimulation system is desired.

The present invention is directed to fully implantable devices and systems that employ multiple implantable components, e.g, a first implantable component housing a rechargeable battery or other replenishable power source, and a second implantable component housing electronic circuitry or devices powered by the replenishable power source.

The present invention also allows different implant configurations to be used as part of the fully implantable system, including, in one embodiment, the ability to use the ICS 112 of the prior systems in a fully implantable system.

Figure 1C:
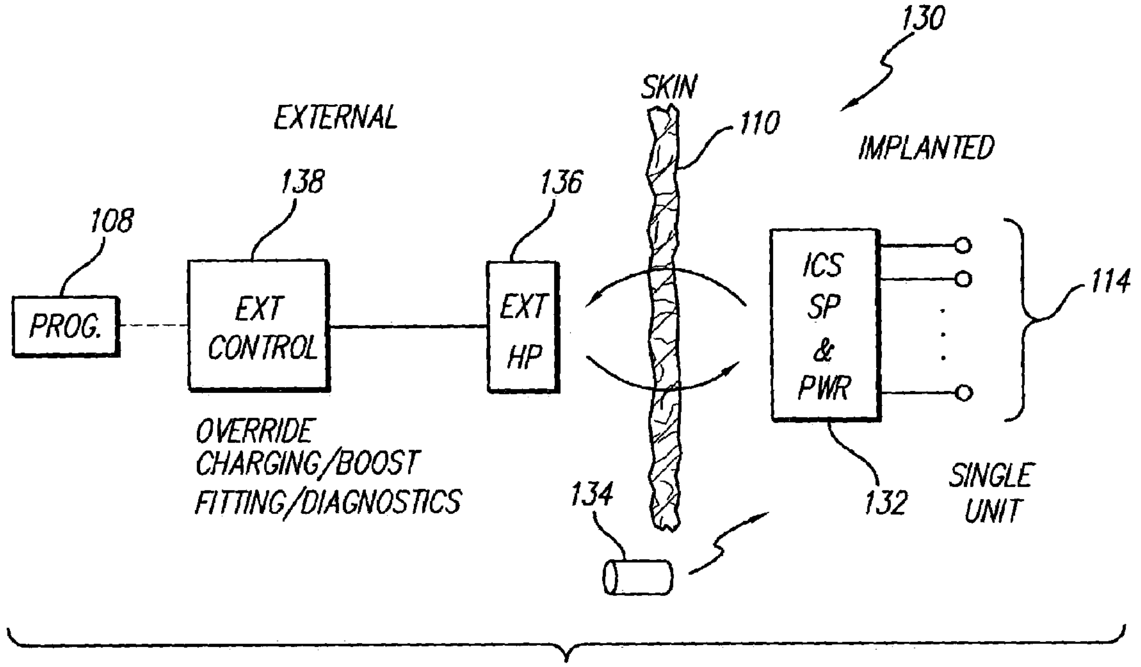
FIG. 1C shows one type of a single unit, fully implantable cochlear stimulation system.

One fully implantable single component system 130 is shown in FIG. 1C. As illustrated in FIG. 1C, such system 130 includes the ICS circuitry, the speech processor circuitry, and a power source within a single unit 132. An electrode array 114 is connected to the single unit 132 in conventional manner. For the embodiment shown in FIG. 1C, a microphone 134 is coupled via a telecoil link to the single unit 132. Such telecoil link powers the microphone circuits through magnetic coupling from the unit 132. Sounds sensed by the microphone 134 are transmitted to the unit 132 via an rf transmitter built-in to the microphone 134. (The transmission distance for such signal is very short, only a centimeter or two, so not much power is needed for such transmission.) Advantageously, such microphone 134 may be inserted inside the ear canal so it is not visible externally.

Other types of microphones may also be used with the implant unit 132. For example, externally-generated sound waves may be sensed through the patient's skin and case shell or wall of the single unit 132 at locations where the case shell or wall is properly supported and of the proper thickness.

When the battery included within the single unit 132 needs to be recharged, which may only be a few minutes a day, or a few times during the week, an external headpiece 136 is placed adjacent the unit 132, and inductive coupling is used to transfer charging power to the unit's battery. The external headpiece, in turn, connects to an external control unit 138, which may, in turn, derive its power from replaceable batteries or from an ac power plug. When programming and/or diagnostic tests are needed, an external programmer 108 may be detachably connected to the external control unit 138.

The external control unit 138 may thus be used to charge/recharge the battery within the implanted unit 132, as well as for other purposes. For example, the external control unit 138 may be used to override the internal speech processor with an external speech processor, e.g., a speech processor included within the external programmer 108. Further, the external control unit 138 may be used to boost the power provided by the internal battery. The external control unit 138 may also be used for programming the implant device 132, e.g., fitting the ICS after implant or adjusting the stimulation parameters of the fully implantable unit 132, as well as for diagnostic purposes.

For the embodiment 130 shown in FIG. 1C, as well as for the other embodiments shown in FIGS. 1D and 1E, discussed below, it is to be understood that backtelemetry may be employed to allow data signals to be sent from the implanted unit to the external headpiece 136, and hence to the external control unit 138.

Figure 1D:
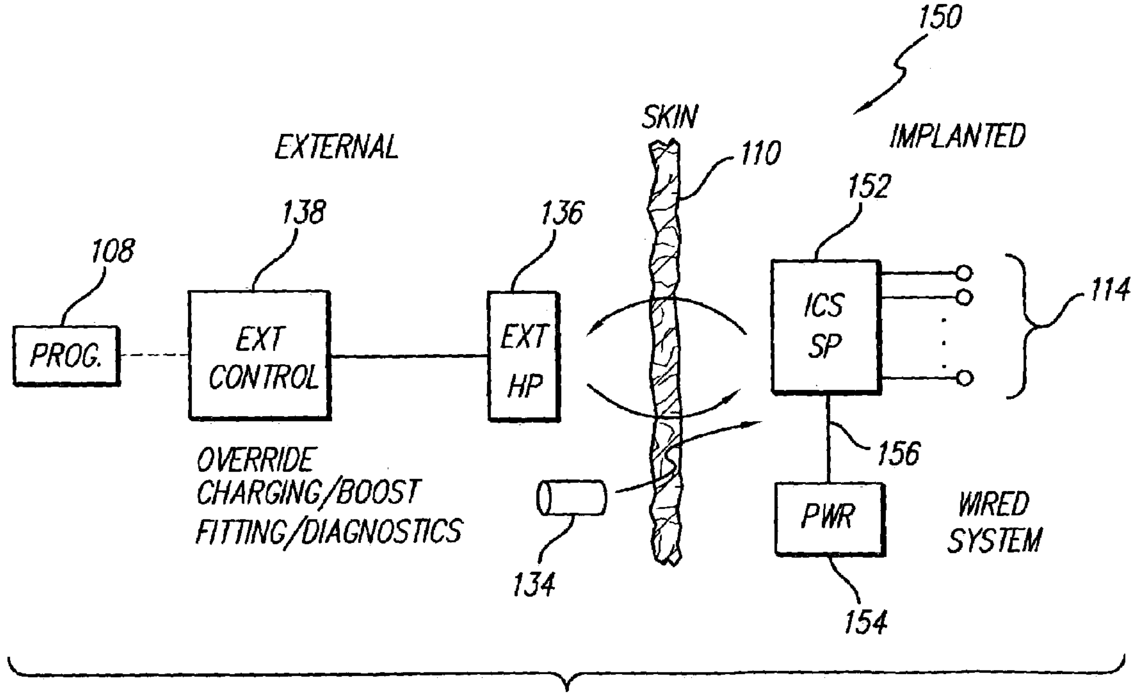
FIG. 1D shows one type of a fully implantable, partitioned, wired system.

Turning next to FIG. 1D, a "wired system" embodiment 150 is depicted. In such wired system 150, at least two separate implantable units 152 and 154 are employed and the circuits of the system are partitioned between the two units. In a first unit 152, for example, speech processor (SP) and ICS circuitry are housed, and such unit is permanently connected to an electrode array 114. In a second unit 154, a battery, or other suitable power source, is housed. The second unit 154 is electrically connected to the first unit 152 via a detachable cable 156. Other embodiments of the partitioned system may, as explained below, place the ICS circuitry in one unit, and the SP and battery in the other unit. Preferably, only ac power should be coupled from the power unit 154 to the other unit 152, thereby preventing any possibility that a dc current might flow through the tissue through which the cable is routed. This is important because a dc current could cause damage to the tissue, whereas an ac current will not. Also, because the cable is not hermetically insulated from the surrounding tissue, it is very possible that minor leakage current could flow through the tissue if it carried dc currents.

The unit 154 includes appropriate switching circuitry that converts the dc power associated with the battery (or other power storage element) therein to an ac signal for coupling to the first unit 152. Also, appropriate circuitry is employed to allow ac power induced into the unit 152 from the external headpiece 136 to be directed to the battery in the unit 154 in order to charge the battery.

Although the preferred power source for use within the fully implantable systems described herein is a rechargeable battery, it is to be understood that other power sources may also be employed. For example, an ultracapacitor (also known as a supercapacitor) may be used. An ultracapacitor, like a conventional capacitor, allows an electric charge (voltage potential) to be stored therein. Unlike a regular capacitor, the energy density of the ultracapacitor is orders of magnitude greater than the energy density of a normal capacitor, thereby allowing a great amount of energy to be stored in the ultracapacitor. This stored energy may then be withdrawn from the ultracapacitor for subsequent use. Thus, for this type of application, where recharging must occur on a regular basis, and when appropriate discharge circuits are employed to control the rate of discharge or energy withdrawal, the ultracapacitor provides a viable alternative to a rechargeable battery for use within the implantable system.

In some embodiments of the invention, a complete-in-cannel (CIC) microphone 134 of the type described previously may be used to sense sounds and couple signals representative of such sounds to the speech processor (SP) circuits within its respective implantable portion.

It should be emphasized that the partitioning illustrated in FIG. 1D, which shows that the ICS and SP circuitry are included within the first implantable unit 152, and which shows that the power source, e.g., rechargeable battery, is included within the second implantable unit 154, is only exemplary. In fact, in one preferred embodiment, the SP circuitry may be included within the second implantable unit 154, leaving only the ICS circuitry within the first implantable unit 152.

The advantage of the wired system 150 shown in FIG. 1D is that a fully implantable system is provided wherein one of the two implantable units, e.g., the power unit 154, may be replaced, if necessary, through only minor surgery. As indicated, the cable 156 that connects the second unit 154 to the first unit 152 is detachable. The implantable connector that connects the cable 156 to the unit 154, may be of any suitable type, e.g., of the type commonly used with implantable pacemakers, or of the pressure type shown in U.S. Pat. No. 4,516,820 (Kuzma), incorporated herein by reference, or of the type shown in U.S. Pat. No. 4,495,917 (Byers), also incorporated herein by reference.

The external headpiece 136 and external control unit 138, and programmer 108, may be used with the wired system embodiment 150 shown in FIG. 1D in the same manner as these components are used with the single unit embodiment 130 shown in FIG. 1C.

Figure 1E:
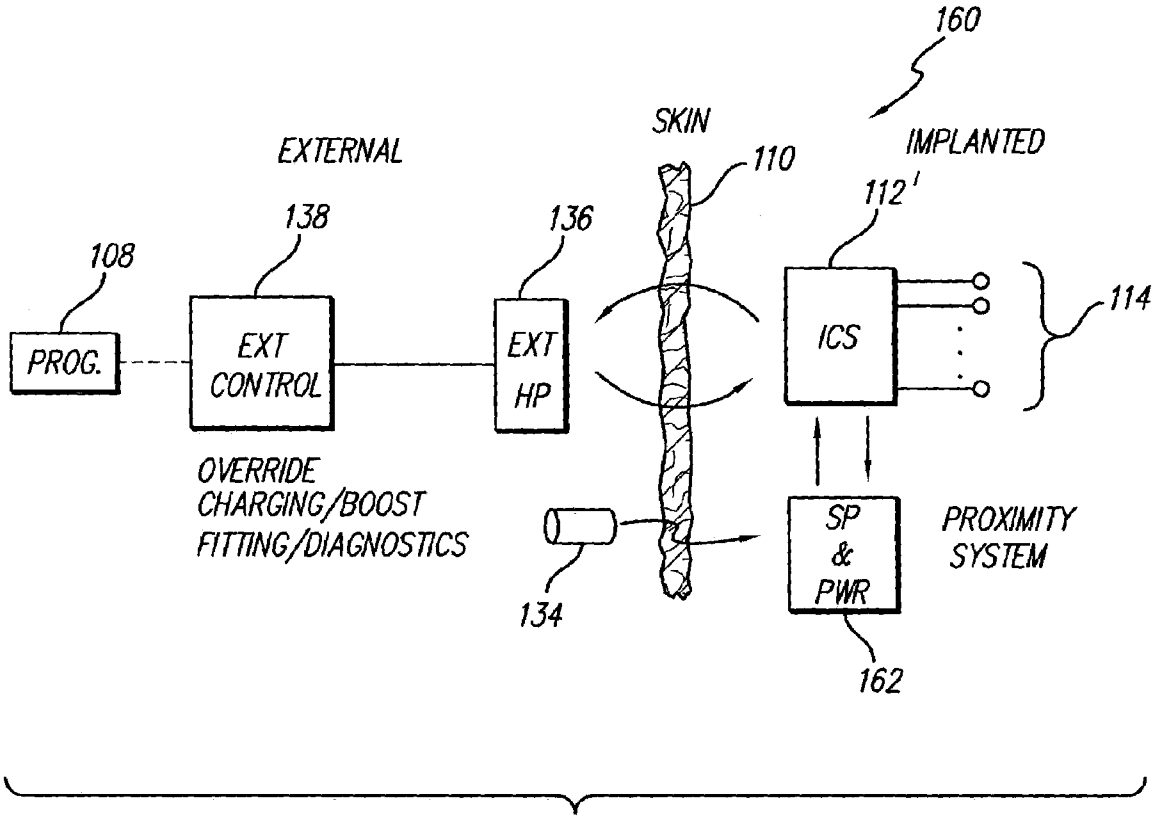
FIG. 1E shows one type of a fully implantable, partitioned, proximity system.

Turning next to FIG. 1E, a partitioned proximity system 160 is shown that is similar to the wired system 150 shown in FIG. 1D, but without the use of a connecting cable 156 connected between the two units. As seen in FIG. 1E, a first implantable unit 112' comprises an ICS with an electrode array 114 connected thereto. An advantage of the proximity system 160 is that the first implantable unit 112' may be substantially the same as, or identical to, that of the ICS 112 used in existing cochlear stimulation systems (see FIG. 1A or FIG. 1B). This allows existing stimulation systems having an ICS 112 to be upgraded to a fully implantable system as shown in FIG. 1E. A second implantable unit 162 includes speech processor (SP) circuits and a power source, e.g., a rechargeable battery. The second unit 162 is implanted so as to be in close proximity to the first unit 112'. As explained in more detail below, one preferred configuration includes a two-conductor cable or lead having one end detachably connected to the unit 162 and having a coil attached at its other end and placed or positioned against or near the first unit 112' so as to be aligned with the coil included within the first unit 112'. An edge channel grove is formed around the periphery of the second unit 162, and provides a convenient channel into which the cable or lead may be wound, like the string of a yo—yo, as the second unit 162 is positioned adjacent the first unit 112'. This allows inductive coupling to occur between the implantable units 112' and 162 in the same manner as occurs between the BTE unit 120 and the ICS 112 shown in FIG. 1B, or between the headpiece 106 and the ICS 112 shown in FIG. 1A.

A suitable microphone, e.g., an complete-in-cannel (CIC) microphone 134 of the type described previously, may be used to sense sounds (pressure waves) and couple electrical signals representative of such sounds to the speech processor (SP) circuits within the implantable portion 162. Alternatively, as described below, a suitable microphone may be fashioned as an integral part of the second unit 162.

The external headpiece 136 and external control unit 138, and programmer 108, may be used with the partitioned proximity system embodiment 160 shown in FIG. 1E in the same manner as used with the single unit embodiment 130 shown in FIG. 1C and the partitioned wired system embodiment 150 shown in FIG. 1D.

With the system shown in FIG. 1E, the following advantages are achieved: (1) older implants, i.e., existing ICS units 112, may be upgraded to fully implantable systems without replacing the implant unit 112 and electrode 114; (2) implantable systems may be upgraded with improved battery (or other power source) technology and lower-power more-sophisticated SP circuits, as such become available, with only minor surgery for the patient; (3) batteries can be replaced with only minor surgery, as required; and (4) charging, override, power boost, fitting and diagnostics may be performed by simply overriding the implanted SP circuits with an external speech processor.

2.0 DESCRIPTION OF THE PREFERRED EMBODIMENTS

With the foregoing as a foundation, a more complete description of one type of fully implantable cochlear implant system (FICIS) will next be described. Three possible configurations of such a FICIS are respectively illustrated in FIGS. 2A, 2B and 2C; and a functional block diagram of such a FICIS is illustrated in FIG. 2D. As seen in these figures, and particularly in FIG. 2D, the FICIS comprises a modularized system that includes various combinations of at least three modules. The three modules include: (1) a small implantable cochlear stimulator (ICS) module 10, with permanently attached cochlear electrode array 12; (2) an implanted speech processor (ISP) module 30, with integrated microphone 32 and rechargeable battery 34; and (3) an external module 50. In one embodiment, the external module 50 comprises an external speech processor (ESP) module. In another embodiment, the external module 50 comprises an external battery charger (EBC) module.

It is noted that the present invention is not directed, per se, to the specific electronic circuitry or electronic componentry used or housed within each of these modules. Any type of suitable circuitry could be used in the modules that performs the functions indicated, or similar functions. Circuitry and componentry suitable for these purposes is disclosed, e.g., in the referenced patents. The present invention, rather, is directed to a system that combines the indicated modules in a way that provides the advantages and benefits enumerated herein.

As schematically seen best in FIG. 2D, the ICS module 10 includes ICS circuitry 14 hermetically sealed in compartment 15. Electrical feed-through pins ("feedthrus") 17 and 19 connect a coil 20 to the ICS circuitry 14. The coil 20 is thus not housed within the hermetically sealed compartment 15, but is embedded within a suitable biocompatible substance 21, e.g., epoxy molding, which is affixed to the walls of the sealed compartment 15. Other feedthrus 22 electrically connect the electrode array 12 to the ICS circuitry 14 through an non-hermetic compartment 23, as explained more fully below in conjunction with FIG. 4C.

The electrode array 12 includes a multiplicity of spaced-apart electrode contacts 13 at its distal end, which electrode contacts are adapted to be placed inside of the cochlea in order to provide an electrical stimulus to the tissue within the cochlea. A typical electrode array 12 may include, e.g., anywhere from 8 to 22 electrode contacts 13.

In addition to the coil 20 which is connected to the feedthrus 17 and 19, one embodiment of the present invention utilizes a two-conductor lead 18 that is electrically connected in parallel with the coil 20. That is, one of the conductors of the lead 18, which may hereafter be referred to as a "pigtail" lead, is electrically connected to the feedthru 17, and the other of the conductors of the lead 18 is electrically connected to the feedthru 19. A jack 25, including, e.g., a tip electrode 24 (connected through one of the conductors of the lead 18 to the feedthru 17) and a ring electrode 26 (connected through the other of the conductors of the lead 18 to the feedthru 19), or other suitable electrode contacts, are located at a distal end of the lead 18.

Still referring to FIG. 2D, it is seen that the ISP module 30 includes an hermetically sealed compartment 31 wherein ISP and other electronic circuitry 33 (hereafter "ISP circuitry" 33) is housed, along with a microphone 32 and a rechargeable battery 34. Feedthrus 35 and 37 electrically connect the ISP circuitry 33 to an electrical connector 36 formed in a suitable biocompatible material, e.g., epoxy molding, affixed to one side or edge of the ISP module 30. Advantageously, the jack 25 at the distal end of the lead 18 may be detachably inserted into the connector 36. When thus inserted, the tip electrode 24 makes electrical contact through feedthru 35 with the ISP circuitry 33, and the ring electrode 26 makes electrical contact through feedthru 37 with the ISP circuitry 33. Those of skill in the art will readily recognize that this type of connector is similar to the basic connectors used in the pacemaker art in order to detachably connect a pacing lead to an implanted pacemaker. See, e.g., U.S. Pat. No. 4,764,132 (Stutz, Jr.) and the art cited therein.

One particular embodiment of the present invention includes the use of an RF lead 18' in place of the pigtail lead 18. As seen in FIG. 2D, the RF lead 18' has a jack 25' at one end, adapted for insertion into the connector 36 of the ISP module 30. At the other end of the lead 18' is an RF coil 26. When used, the coil 26 of the RF lead 18' is positioned as close as possible to, and in alignment with, the coil 20 embedded within the molded epoxy 21 of the ICS module 10. See FIG. 3B for a more detailed explanation of how this alignment is achieved. Moreover, in one preferred embodiment, it is noted that not only is the pigtail lead 18 not used, but the coil 20' is connected directly through feedthru terminals 35 and 37 to the ISP 33, thereby obviating the need for the connector 36. When connected directly to the terminals 35 and 37 in this manner, the coil 20' may be embedded within a suitable biocompatible substance, such as the biocompatible substance 21 within which the coil 20 is embedded. Hence, in such preferred embodiment, it is seen that the hermetically-sealed module 31 is coupled directly to hermetically-sealed module 15 through coils 20' and 20. Neither coil 20' nor coil 20 is hermetically sealed, but each may be carried in a suitable biocompatible substance so as to be mechanically attached to its respective module. Each coil 20' or 20 is electrically connected to the circuitry within the respective hermetically-sealed compartments through suitable feedthru pins 35 and 37 (module 31) or 17 and 19 (module 15).

As seen in FIG. 2D, both the ICS module 10 and the ISP module 30 are adapted to be implanted beneath the skin layer 110 of the patient. When the battery 34 has sufficient charge stored therein, the operation of the ICS module 10 and ISP module 30 proceeds without assistance from any external components. Thus, the system created by the ICS module 10 and ISP module 30 is self-sufficient, and truly becomes a fully implantable cochlear implant system that provides the patient with the sensation of hearing.

As needed, the fully implantable system may be assisted or boosted with an external module 50. Such external module 50 may be needed, e.g., to charge the battery 34, or to override the ISP circuitry 33 with external speech processing controls and commands. Such external module 50 includes a headpiece 50', having a coil 52 therein. In some embodiments, the headpiece 50' may also include an external microphone. The headpiece 50' is connected to an external unit 54, which external unit comprises appropriate electronic circuitry, e.g, an external speech process (ESP) or an external battery charger (EBC). The external unit 54, in turn, is powered from an external power source 56. Typically, the external power source will comprise a replaceable battery. However, the external power source could conceivably be any available power source, including batteries, including either replaceable or rechargeable batteries; charged super capacitors; dc power supplies connected to the ac line voltage (110 vac, 60 Hz); solar panels; hand-operated generators; or the like.

Figure 2A:
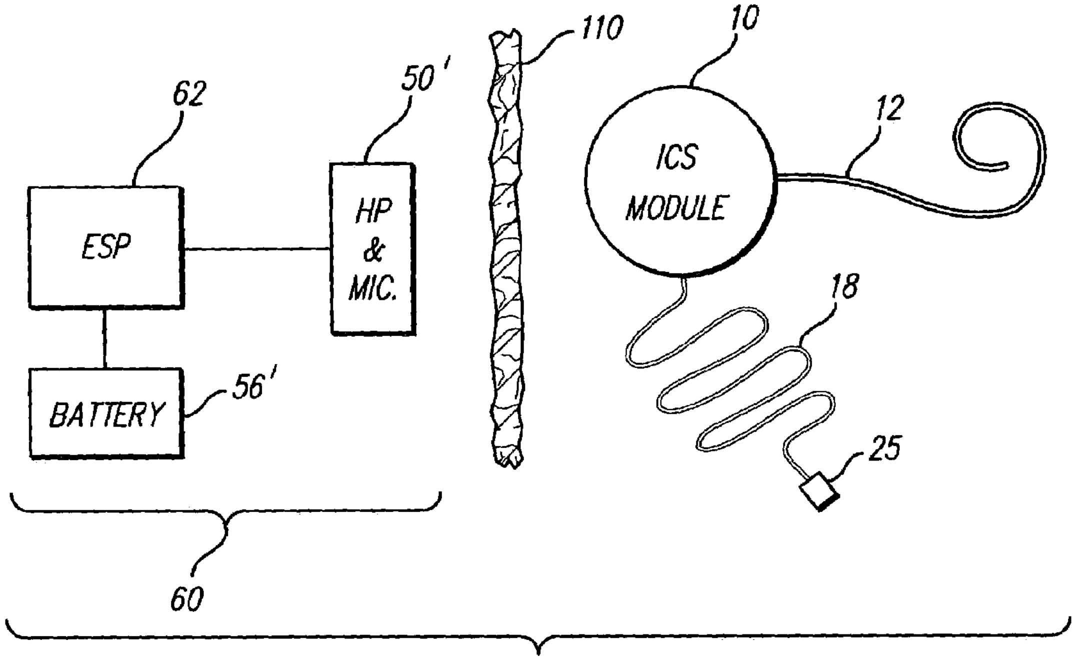
FIGS. 2A, 2B and 2C illustrate, respectively, three different configurations that may be realized using modularized fully implantable cochlear implant systems.

FIG. 2A illustrates one variation of the invention that is particularly well suited for young children. This variation includes an ICS module 10 used with an ESP module 60. The ESP module 60 includes a headpiece and microphone 50', an external speech processor 62 and related circuitry, powered by a battery 56'. As such, the variation shown in FIG. 2A is similar to existing cochlear stimulation systems (see, e.g., FIG. 1A). The configuration shown in FIG. 2A is especially suited for small children where the head size and bone thickness cannot accommodate the entire FICIS system. The primary goal of this configuration is to upgrade it to a fully implantable system once the patient has grown sufficiently so that the head size and bone thickness are no longer a limitation.

The advantage of the variation shown in FIG. 2A is that in can readily be upgraded to a fully implantable system at a later date by adding an ISP module 30. The ISP module 30 may be added using either of two approaches. In a first approach, an ICS module 10 with pigtail lead 18 is first implanted, with the pigtail lead 18 not being used, as shown in FIG. 2A. That is, the jack 25 at the distal end of the pigtail lead 18 is not connected to anything when the ICS module 10 is first implanted. Typically, the jack 25 will be protected with a suitable insulating protective cover or sleeve. Such unused pigtail lead 18 may, in some instances, be wrapped around a "dummy" ISP module, which dummy ISP module would preserve a space within the pocket formed under the skin for the later-implanted real ISP module 30. In small children, however, such "dummy" module would likely not be used, but rather the pigtail lead 18, with protective sleeve, would simply be coiled under the skin in the region where the later-implanted ISP module would eventually be located. Then, at a later date, when the ISP module 30 is implanted, the pigtail lead 18 may be be extracted through an incision, connected to a new ISP module 30, and the ISP module 30 could then be implanted, coiling the pigtail lead 18 around it, as described below.

In a second approach, the ICS module 10, with or without a pigtail lead, is implanted first. Then, at a later date, when the ISP module 30 is to be implanted, an incision is made next to the ICS module 10 and a pocket is formed under the skin. An RF lead 18' is connected to the ISP module 30 by way of the connector 36. The coil 26 at the other end of the RF lead 18' is pushed into the pocket and positioned adjacent to and aligned with the embedded RF coil 20 of the ICS module 10. The ISP module 30 is then inserted into the pocket with a rotation movement so as to wind the lead 18' around the edge of the module as it is inserted. An edge channel grove is provided around the periphery of the ISP module 30 to facilitate this process. The incision that opens into the pocket is then closed with appropriate suturing or other means.

Figure 2B:
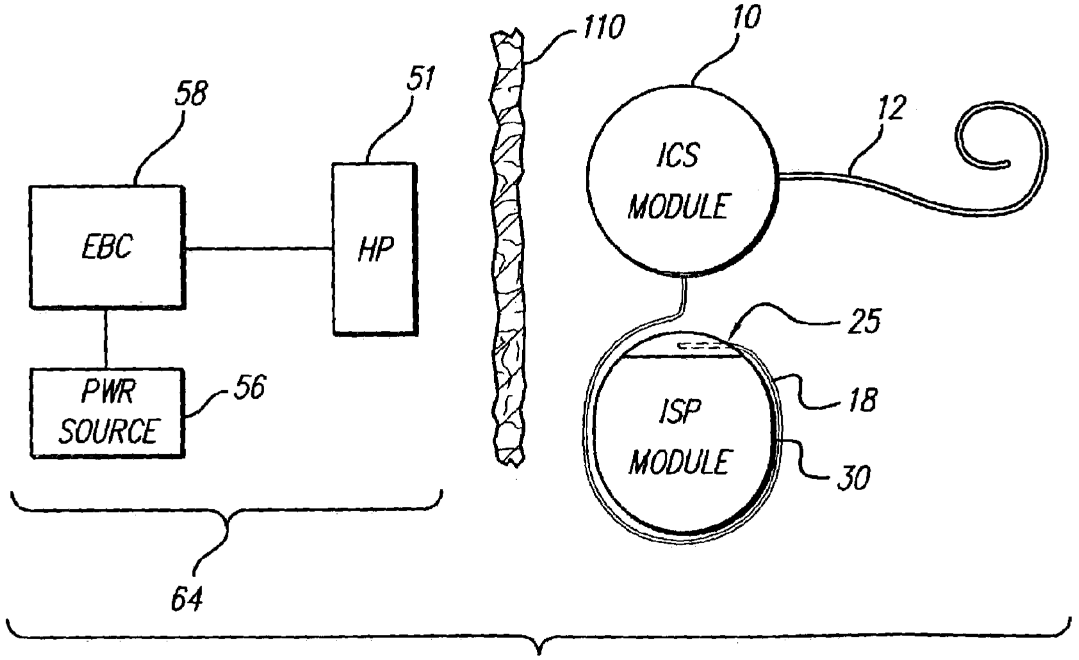

As seen in FIG. 2B, a second configuration of the invention uses an ICS module 10 with an ISP module 30. Periodic recharging of the battery 34 within the ISP module 30 is performed using an external module 64 that includes a headpiece 51, an external battery charger (EBC) 58, and an external power source 56. The configuration shown in FIG. 2B represents a fully implantable system that is self-sufficient for as long as the battery 34 in the ISP module remains charged. Typically, such battery 34 should last, under normal use, for at least two days. The battery 34, of course, requires periodic recharging, which recharging may preferably occur overnight during sleep using the EBC 58 and related components.

Figure 2C:
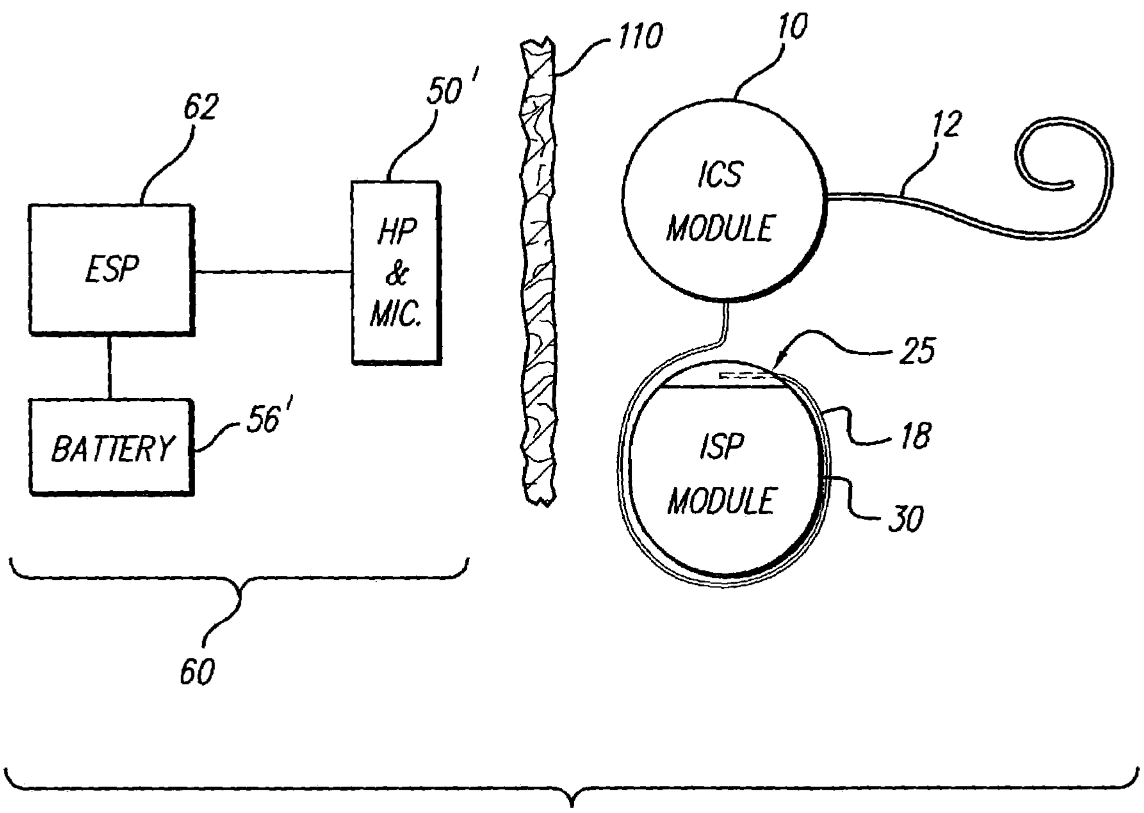
Figure 2D:
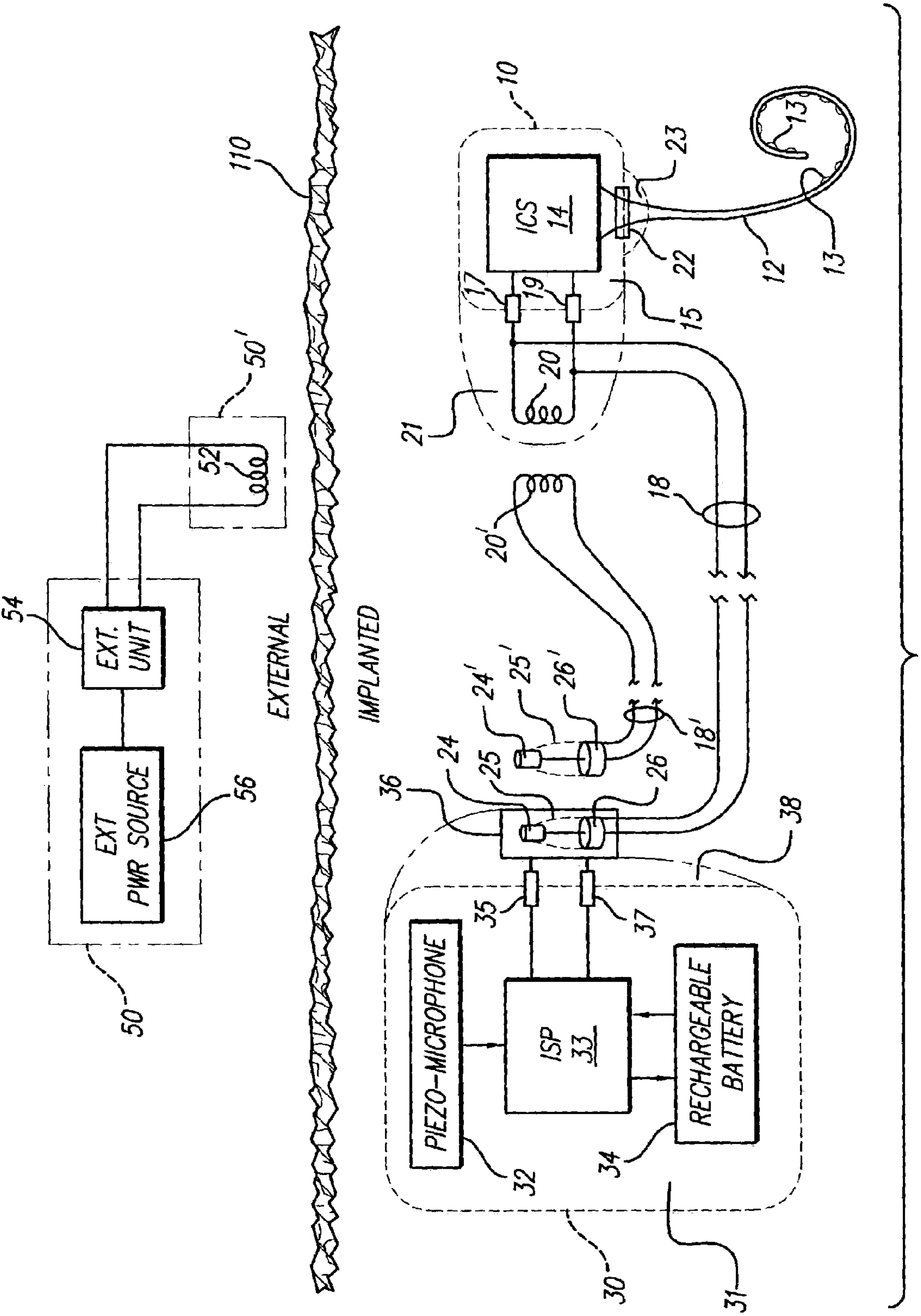
FIG. 2D is a schematic block diagram of one type of fully implantable cochlear implant system.

Turning next to FIG. 2C, a third configuration of the invention uses an ICS module 10 with an ISP module 30 with assistance from an external speech processor (ESP) module 60. The ESP module 60 is essentially the same as that described above in connection with FIG. 2A. Such module 60 is used to drive (control) the ICS module 10 and at the same time apply a slow charge to the implanted battery 34 contained within the ISP module 30. The ESP module 60 may be used jointly with the internal speech processor 33 contained within the ISP module 30, or alternatively to take over the function of the internal speech processor should it malfunction or otherwise require replacement.

Figure 3A:
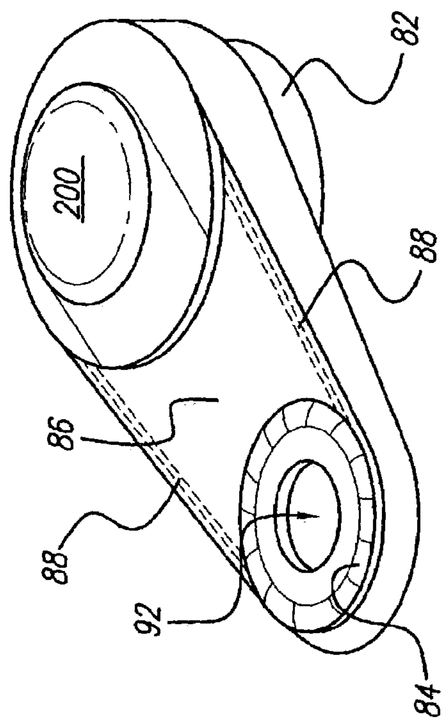
FIG. 3A depicts a perspective view of one unit or device of an implantable system made in accordance with one of several embodiments of the invention.
Figure 3B:
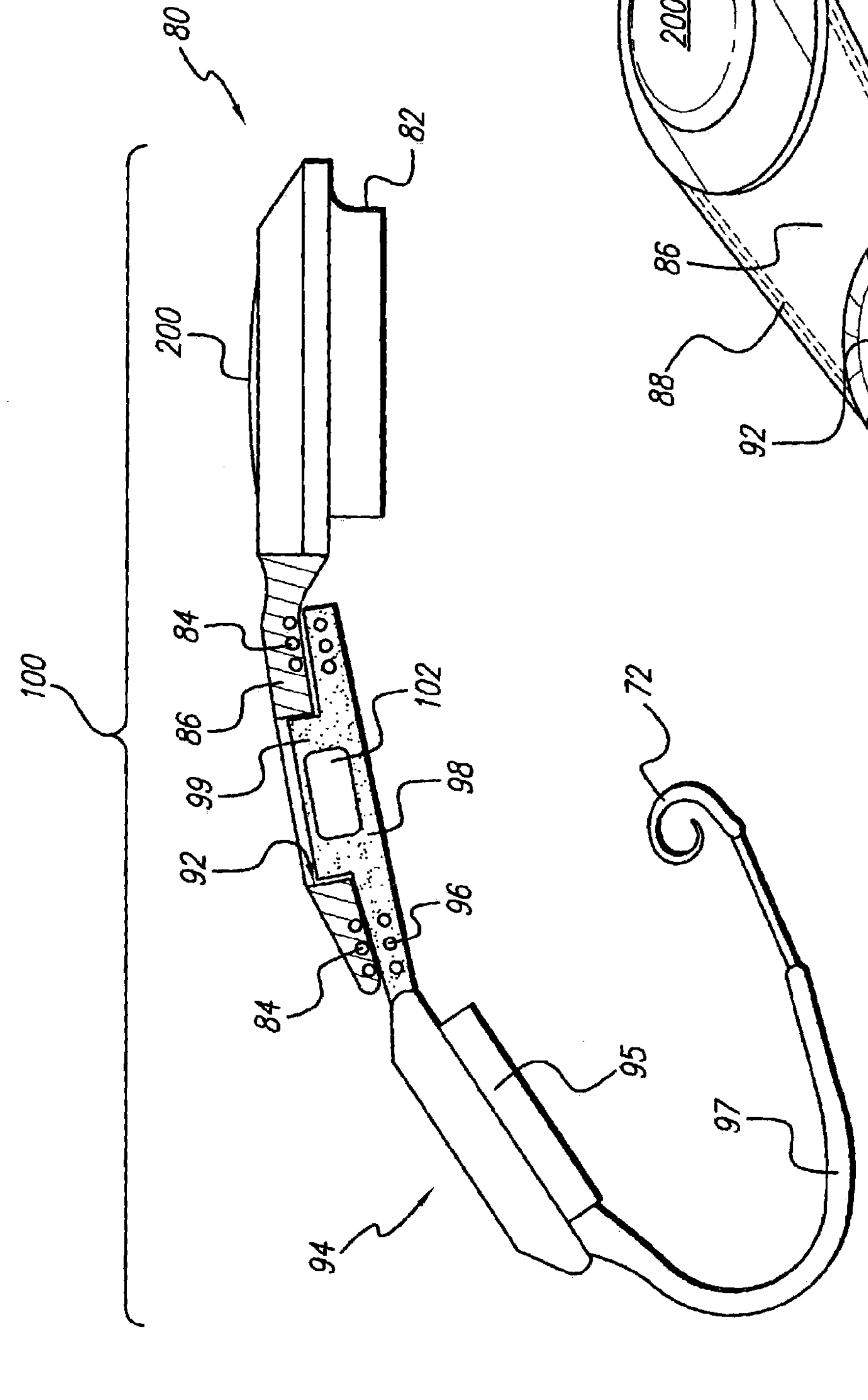
FIG. 3B illustrates the unit of FIG. 3A coupled with another implantable unit of the implantable system, i.e., an implantable cochlear stimulator (ICS) and cochlear electrode array, to form a fully implantable cochlear system.

Next, with reference to FIGS. 3A, 3B and 3C, one particular preferred embodiment for electrically and mechanically coupling two implantable modules together is illustrated.

FIG. 3A depicts a perspective view of one implantable module 80 of a two-module implantable system. The module 80 includes a built-in microphone assembly. (The microphone assembly is not part of the present invention, but is described only as an example of one type of function that may be carried out within an implantable module.) The module 80 has an hermetically-sealed case 82 to which a microphone diaphragm 200 has been mounted. An antenna coil 84 is also attached to the case 82. The antenna coil 84, which may be used both for transmitting and receiving electromagnetic or rf signals, is embedded within a silicone antenna molding 86. The silicone molding 86 is mechanically attached to the case 82. The antenna coil 84 has wires 88 that are electrically connected to electronic circuitry contained within the sealed case 82 by way of an hermetically-sealed feed-through terminal. The antenna molding 86 further has a locking hole 92 formed therein, e.g., so as to reside in the center of the antenna coil 84.

FIG. 3B illustrates the implantable module 80 coupled with an implantable cochlear stimulator (ICS) 94 and cochlear electrode array 72 to form a fully implantable cochlear system (FICS) 100. The ICS 94 also includes an hermetically sealed case 95 in which electronic components associated with the operation of the ICS are housed. A multi-conductor cable 97 connects with the electrode array 72. A coil 96 is electrically connected to the circuitry within the ICS case 95 and is embedded within a silicone molding 98. The coil 96, as well as the multiple conductors of the cable 97, are electrically connected to the electronic circuitry contained within the ICS 94 by way of feed through terminals (not shown in FIG. 3B).

The silicone molding 98 of the ICS 94 includes a knob portion 99 that is centrally located relative to the coil 96. The silicone knob portion 99 is sized to fit within the hole 92 formed in the molding 86 of the implantable device 80. Thus, when the knob portion 99 is placed within the hole 92, the antenna coil 84 of the module 80 is coaxially aligned with the coil 96 of the ICS 94.

Advantageously, as long as the knob 99 of the silicone mold 98 remains inserted within the hole 92 of the silicone mold 92, the coaxial alignment between the coils 84 and 96 is locked. When the coils 84 and 96 are coaxially aligned in this fashion, it is possible for electrical signals to be inductively coupled from one coil to the other, just like signals are inductively coupled from one coil to another in a transformer. Hence, control signals and power may be coupled from the implantable module 80, which may be, e.g., an implantable speech processor, to the ICS 94. The ICS 94, in turn, responds to such control signals in a programmed manner so as to provide electrical stimuli to selected electrodes included as part of the electrode array 72, thereby directly electrically stimulating the auditory nerve of the user, and providing the user with the sensation of hearing.

Moreover, it is possible for a third coil (not shown in FIG. 3B) that is held in alignment with the coils 84 and 96 to also couple signals to and from the coils 84 and 96. A magnet 102, embedded or carried within the molded knob 99, may be used to help align, and maintain the alignment of, such third coil. Thus, when the fully implantable cochlear system (FICS) 100 is implanted in a user, including the coils 84 and 96 and their respective silicone molds 86 and 98, then an external coil, e.g., a coil that is part of an external headpiece or an external charging pad, may be held against the skin of the user above the location where the coils are implanted. Such external coil is held in alignment with the implanted coils 84 and 96 by the magnet 102. When so positioned, electrical communication from an external location may be readily established with the implanted FICS 100, thereby permitting programming and/or recharging of the FICS to occur.

Thus, it is seen that FIG. 3B illustrates an implantable system that includes a plurality of implantable devices that are detachably coupled to each other. Each implantable device of the system includes: (1) an hermetically-sealed case housing electronic components; (2) feedthrough terminals mounted to a wall of the hermetically-sealed case adapted to allow electrical contact from a location outside the hermetically-sealed case with the electronic components housed inside the hermetically-sealed case; (3) a coil external to the hermetically-sealed case attached to the feedthrough terminals; (4) a flexible molding bonded to the hermetically-sealed case, and wherein the coil is embedded within or otherwise attached to the flexible molding; and (5) engagement means for engaging the flexible molding with a flexible molding of another implantable device of the implantable system. Such engagement means also advantageously aligns the coils of the implantable devices that are thus engaged with the engaging means to allow electromagnetic coupling to occur between the aligned coils.

It should be pointed out that the hole-knob engagement means illustrated in FIG. 3B to couple the two implantable devices or modules together so that their respective coils are aligned is only representative of numerous different types of engagement means that may be employed as part of the invention. Any suitable engagement means within or between the flexible moldings 86 or 98 of the two implantable devices may be used. For example, any type of keyed engagement mechanism may be used that detachably secures the two moldings together in a way that assures the respective coils are aligned and that the implantable devices have a fixed relationship with each other, such as a square- or rectangular-shaped hole, and a correspondingly-shaped knob. Multiple holes arranged in a pattern in one molding, with corresponding stubs or pins adapted to fit into respective holes in the other molding, may likewise be used. Also, miniature disk magnets embedded in a pattern within one molding, along with corresponding miniature magnets embedded in the same pattern in the other molding, and with the polarity of the magnets arranged to assure attraction when the proper alignment is achieved, may also be used. A sliding tongue and groove engagement mechanism may also be used, e.g., wherein the flexible molding of a first implantable device is configured with a groove, into which a tongue configured in the flexible molding of the second implantable device is adapted to be slidably engaged.

Figure 4:
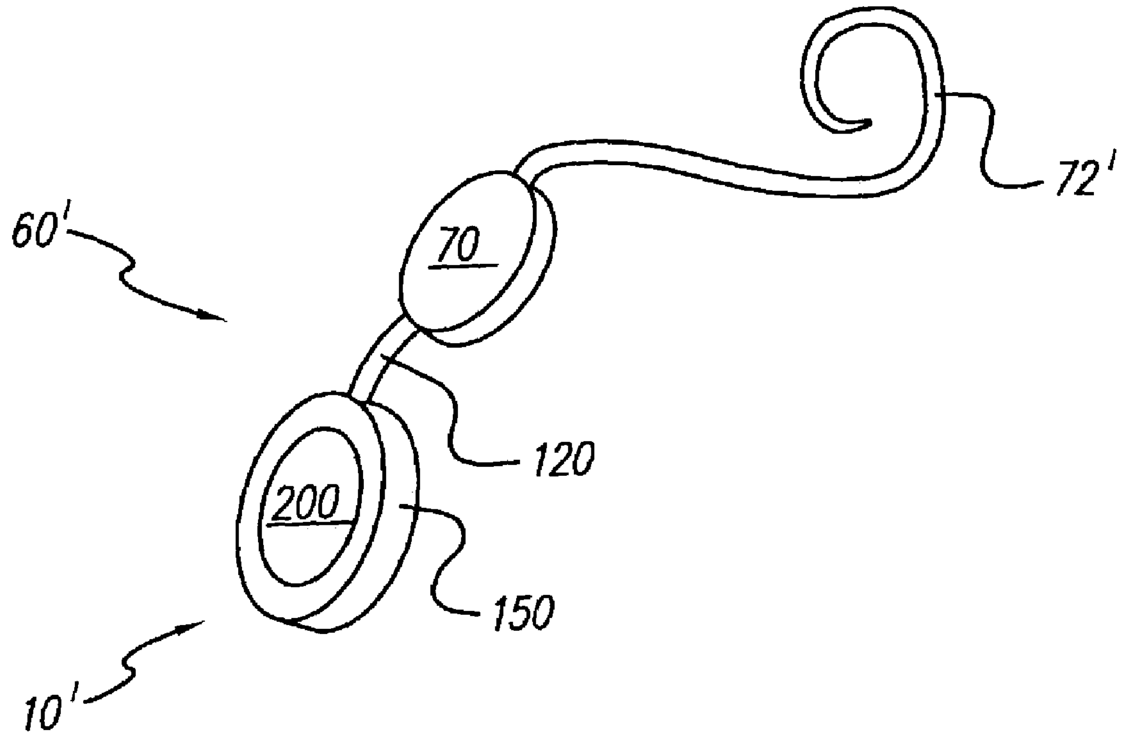
FIG. 4 shows another embodiment of a fully implantable cochlear system (FICS).

Turning next to FIG. 4, there is shown another representation (in addition to that shown in FIGS. 1D, 2B, 2C and 2D) of how one implantable module, including one having an implantable microphone assembly, may be used as part of a fully implantable cochlear system (FICS) 60'. As seen in FIG. 4, the FICS includes an implantable device 10' having a microphone diaphragm 200 mounted to its case 150. Such device 10' further includes, in addition to a battery 30, all of the circuit components needed to perform a desired speech processing function. As thus configured, the module 10' functions as an implantable speech processor (ISP).

The ISP device 10' is coupled, e.g., through cable 120, to another implantable device or module 70. The implantable device 70 comprises, e.g., an implantable cochlear stimulator (ICS) that includes pulse generation circuitry adapted to respond to control signals and power received from the ISP module 10', and to present electrical stimuli on selected electrodes of a cochlear electrode array 72'. The electrode array 72' is adapted to be inserted into the cochlea of a user. Hence, electrical stimuli generated by the ICS device 70, which is in response to sound waves sensed through the implantable microphone assembly that forms part of the ISP module 10', can directly electrically stimulate the user's auditory nerve, and thereby provide the user with the ability to perceive sound.

While the invention herein disclosed has been described by means of specific embodiments and applications thereof, numerous modifications and variations could be made thereto by those skilled in the art without departing from the scope of the invention set forth in the claims.

What is claimed is:

1. A method of configuring an implantable system comprising:

(a) partitioning the functions of the implantable system into a plurality of implantable modules; and (b) inductively coupling the plurality of implantable modules to each other, wherein the inductive coupling comprises:

connecting a coil to each module, wherein the coil is electrically connected to electrical components housed within each module;

positioning the coils of each module so that they are aligned with each other so as to allow electromagnetic coupling to occur been the aligned coils;

embedding the coils in a flexible molding attached to each module; and engaging the flexible molding in which a first coil of a first implantable module is embedded with the flexible molding of a second coil of a second implantable module, wherein the engaging comprises:

aligning the first and second coils;

forming a hole in the flexible molding of the first implantable module;

forming a knob in the flexible molding of the second implantable module, wherein the knob has a size and shape adapted to permit the knob to be detachably inserted into the hole, and wherein when the knob is inserted into the hole the first and second coils are aligned; and inserting the knob into the hole.

2. The method of claim 1, wherein engaging the flexible molding of the first coil with the second coil further includes embedding a magnet within the knob of the second implantable module, wherein the magnet allows an additional coil to be aligned with the coils of the first and second implantable modules.

3. The method of claim 1, wherein engaging the flexible molding of the first coil with the second coil further includes forming the hole and the knob to include keyed portions, whereby the knob may be inserted into the hole only when a desired orientation is established between the first and second implantable modules.

4. A method of making an implantable system comprising steps for:

(a) partitioning the implantable system into a plurality of implantable modules, each module having an hermetically-sealed case wherein electrical components associated with each module are housed;

(b) providing electrical feedthru terminals that allow electrical connection to be made between the electrical components inside the hermetically-sealed case of each module with a terminal pin on the outside of the hermetically-sealed case;

(c) attaching a coil to each of the plurality of modules, wherein each coil is external to the hermetically-sealed case of each module, and wherein each coil is electrically connected through the feedthru terminal pins with the electrical components on the inside the hermetically-sealed case; and (d) aligning the coils of each module with each other when the modules are implanted, wherein such aligning comprises:

embedding the coils in a flexible molding attached to each module;

forming a hole in the flexible molding of a first implantable module;

forming a knob in the flexible molding of a second implantable module, wherein the knob has a size and shape adapted to permit the knob to be detachably inserted into the hole, and wherein when the knob is inserted into the hole the coil of the first implantable module is aligned with the coil of the second implantable module; and inserting the knob into the hole.

5. The method of claim 4, wherein aligning the coils of each module with each other further includes embedding a magnet within the knob of the second implantable module, wherein the magnet allows an additional coil of an external module to be aligned with the coils of the first and second implantable modules.

6. The method of claim 4, wherein aligning the coils of each module with each other further includes forming the hole and the knob to include keyed portions, whereby the knob may be inserted into the hole only when a desired orientation is established between the first and second implantable modules.

7. An implantable system comprising a plurality of implantable devices detachably coupled to each other, each implantable device comprising:

an hermetically-sealed case housing electronic components;

feedthrough terminals mounted to a wall of the hermetically-sealed case adapted to allow electrical contact from a location outside the hermetically-sealed case with the electronic components housed inside the hermetically-sealed case;

a coil external to the hermetically-sealed case attached to the feedthrough terminals;

a first flexible molding bonded to the hermetically-sealed case, and wherein the coil is embedded within the first flexible molding; and engagement means for engaging the first flexible molding with a second flexible molding of another implantable device of the implantable system, wherein the engagement means also aligns the coils of the implantable devices that are engaged with the engaging means to allow electromagnetic coupling between the aligned coils, wherein engagement means comprises:

a hole in the first flexible molding of a first implantable device and a knob in the second flexible molding of a second implantable device, and wherein the knob has a size and shape adapted to permit the knob to be detachably inserted into the hole, and wherein when the knob is inserted into the hole the coils of the first and second implantable devices are aligned with each other, thereby permitting electrical signals to be transferred through electromagnetic coupling between the coils of the first and second implantable devices.

8. The implantable system of claim 7, wherein the engagement means further includes a magnet embedded within the knob of the second implantable device, wherein the magnet provides a means for aligning an additional coil with the coils of the first and second implantable devices.

9. The implantable system of claim 7 wherein the knob and the hole further include keyed portions that permit the knob to be inserted into the hole only when a desired orientation is established between the first and second implantable devices.

10. The implantable system of claim 7 wherein the hole comprises a square or rectangular-shaped hole, and the knob comprises a correspondingly-shaped knob.

11. The implantable system of claim 7 wherein multiple holes are arranged in a pattern in the first flexible molding, and wherein a corresponding pattern of stubs or pins are formed in the second flexible molding, and wherein the stubs or pins of the second flexible molding are adapted to fit into the respective holes in the first flexible molding.

12. The implantable system of claim 7 wherein the first flexible molding further includes miniature disk magnets embedded in a pattern, and wherein the second flexible molding further includes corresponding miniature magnets embedded in the same pattern, and wherein the polarity of the magnets in the second flexible molding is arranged to assure attraction to the magnets in the first flexible molding when a proper alignment is achieved between the first and second flexible moldings.

13. The implantable system of claim 7 wherein the engagement means further comprises a sliding tongue and a groove engagement mechanism, wherein the first flexible molding of the first implantable device is configured with the groove, and wherein the second flexible molding of the second implantable device is configured with the tongue, and wherein the tongue is adapted to be slidably engaged with the groove.

* * * * *